United States Patent [19]

Nakazawa et al.

[11] Patent Number: 5,214,053
[45] Date of Patent: May 25, 1993

[54] THIOUREA DERIVATIVES AND ANTIMICROBIAL AGENT AND ANTIULCER AGENT CONTAINING THE SAME

[75] Inventors: Keiichi Nakazawa, Hadano; Masashi Isozaki, Odawara; Shingo Koyama, Hadano, all of Japan

[73] Assignee: Terumo Kabushiki Kaisha, Tokyo, Japan

[21] Appl. No.: 939,692

[22] Filed: Sep. 2, 1992

[30] Foreign Application Priority Data

Sep. 6, 1991 [JP] Japan .................................. 3-227466

[51] Int. Cl.$^5$ ............................................ C07D 211/06
[52] U.S. Cl. ...................... 514/318; 514/321; 514/452; 514/464; 546/194; 546/197; 549/362; 549/365
[58] Field of Search ............... 546/194, 197; 549/362, 549/365; 514/318, 321, 452, 464

[56] References Cited

U.S. PATENT DOCUMENTS 3,950,537  4/1976  DeBenneville et al. ............ 514/587

FOREIGN PATENT DOCUMENTS

0470006A1  2/1992  European Pat. Off. ................ 335/8
WO87/05902  10/1987  World Int. Prop. O. ............ 407/12

OTHER PUBLICATIONS

Chemical Abstracts; 98:143139; Apr. 25, 1983.

*Primary Examiner*—Marianne M. Cintins
*Assistant Examiner*—Michael Hydorn
*Attorney, Agent, or Firm*—Burns, Doane, Swecker & Mathis

[57] ABSTRACT

Thiourea derivatives represented by the formula (I)

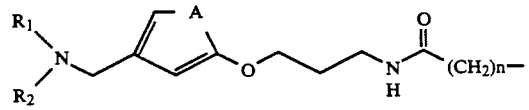

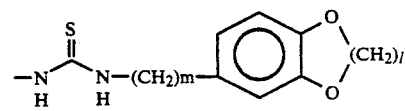

wherein $R_1$ and $R_2$ are the same or different and each represents a lower alkyl group, or $R_1$ and $R_2$ taken together represent a group having the formula $-(CH_2)_x-CHR_3-(CH_2)_y-$ in which $R_3$ represents hydrogen or a lower alkyl group and x and y represent an integer of 0 to 2, respectively, A represents the formula $-CH=CH-$ or $-CH=N-$, l is 1 or 2, m represents an integer of 0 to 2 and n represents an integer of 1 to 5.

The thiourea derivatives possess an antiulcer activity and an antimicrobial activity against *Helicobacter pyroli* and are useful as an antiulcer agent and an antimicrobial agent against *Helicobacter pyroli*.

20 Claims, No Drawings

THIOUREA DERIVATIVES AND ANTIMICROBIAL AGENT AND ANTIULCER AGENT CONTAINING THE SAME

BACKGROUND OF THE INVENTION

1. Field of the Invention

This invention relates to novel thiourea derivatives and an antimicrobial agent against *Helicobacter pylori* and an antiulcer agent containing the same.

2. Description of the Prior Art

As a result of the development of histamine $H_2$ antagonists, the therapy of peptic ulcers has become easier. However, it is now a big problem that the high incidence of recurrence of the disease after discontinuing the administration of the drug still remains. Since the recurrence of the ulcers is believed to be due to decrease in the gastric defense factors during inhibition of the gastric acid secretion, it is hoped to develop a drug concurrently possessing a gastric antisecretory activity and an activity of reinforcing the gastric defense factors. Furthermore, it has recently been found that growth of *Helicobactor pylori* occurs in a high incidence in the attention has been drawn to the relation of the microorganism with recurrence of peptic ulcers. This suggests that a drug which has an antimicrobial activity against *Helicobacter pylori* would prevent the recurrence of peptic ulcers.

SUMMARY OF THE INVENTION

As a result of extensive studies on the synthesis and physiological action of various thiourea derivatives, we have found that the thiourea derivatives of the present invention possess not only high gastric antisecretory and gastric defense factor-reinforcing activities but also an anti-microbial activity against *Helicobacter pyroli*. The instant invention is based upon the above findings. The thiourea derivatives of the invention are useful in the therapy of peptic ulcers.

Therefore, it is an object of the invention to provide thiourea derivatives having said valuable activities.

Another object of the invention is to provide an antimicrobial agent containing said thiourea derivatives.

Further object of the invention is to provide an antiulcer agent containing said thiourea derivatives.

DETAILED DESCRIPTION OF THE INVENTION

In accordance with the present invention there are provided thiourea derivatives represented by the formula (I)

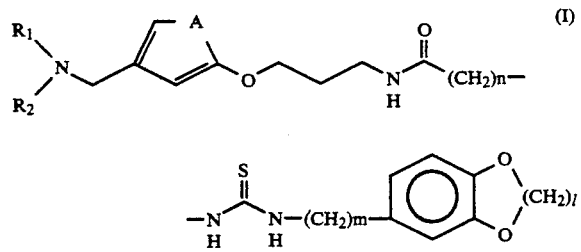

wherein $R_1$ and $R_2$ are the same or different and each represents a lower alkyl group, or $R_1$ and $R_2$ taken together represent a group having the formula $-(CH_2)_x-CHR_3-(CH_2)_y-$ in which $R_3$ represents hydrogen or a lower alkyl group and x and y represent an integer of 0 to 2, respectively, A represents the formula $-CH=CH-$ or $-CH=N-$, l is 1 or 2, m represents an integer of 0 to 2 and n represents an integer of 1 to 5.

In the above definitions, lower alkyl means a straight or branched alkyl group having 1-4 carbon atoms, for example, methyl, ethyl, n-propyl, isopropyl, n-butyl, isobutyl, tert.-butyl.

Preferred compounds of the present invention are as follows:

The thiourea derivative of the formula (I) wherein $R_1$ and $R_2$ taken together represent a group having the formula $-(CH_2)_x-CHR_3-(CH_2)_y-$ in which $R_3$ is a hydrogen atom or a methyl group, x and y are 1 or 2, respectively, A represents the formula $-CH=CH-$, l is 1 or 2, m is 0 or 1 and n is 3 or 5.

The thiourea derivative of the formula (I) wherein $R_1$ and $R_2$ taken together represent a group having the formula $-(CH_2)_xCHR_3-(CH_2)_y-$ in which $R_3$ is a hydrogen atom, x and y are 2, respectively, A represents the formula $-CH=N-$, l is 1, m is 0 and n is 3.

The thiourea derivative of the formula (I) wherein $R_1$ and $R_2$ are ethyl group, respectively, A represents the formula $-CH=CH-$, l is 1, m is 0 and n is 3.

The invention is also directed to an antimicrobial agent against *Helicobacter pyroli* and an antiulcer agent containing thiourea derivatives represented by the above-mentioned formula (I) or physiologically acceptable salts thereof.

The thiourea derivatives represented by the above-mentioned formula (I) are produced by reacting an amine derivative represented by the formula (II)

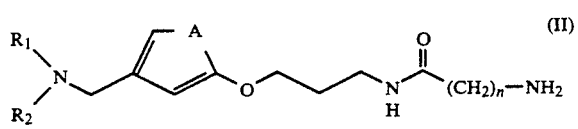

wherein $R_1$ and $R_2$ and n have the same meanings as defined above with an isothiocyanate derivative represented by the formula (III)

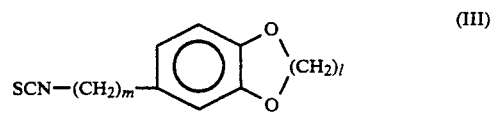

wherein l and m have the same meanings as defined above preferably in a solvent.

Reaction solvents that may be used includes ethanol, methanol, methylene chloride and chloroform. The reaction may desirably be carried out at a temperature between 0° C. and a refluxing temperature of a solvent used in the reaction for from one hour to 20 hours.

The novel thiourea derivatives of the invention are used an antimicrobial agent against *Helicobacter pylori* or an antiulcer agent, dosage levels of which may be varied depending upon the symptoms and are generally 10–2000 mg, preferably 20–600 mg per day for adults. The daily dose may be divided into 1–3 doses, if required in accordance with the symptoms.

The compounds of the invention can be administered in any form suitable for the administration. Oral administration is especially desirable, but intravenous injection is feasible.

The compounds of the invention as an active ingredient or one of active ingredients are formulated alone or in admixture with pharmaceutical carriers or excipients by a conventional method into various forms such as tablets, sugar-coated tablets, powders, capsules, granules, suspension, emulsion, injectable solution or the like.

As examples of the carrier or excipient, there may be mentioned calcium carbonate, calcium phosphate, starch, glucose, lactose, alginic acid, mannitol, talc, magnesium stearate and the like.

The invention will be described in more detail below with reference to examples and test examples. These examples, however, should not be construed as limiting the invention.

EXAMPLE 1

To a solution of N-[3-[3-(pyperidinomethyl)phenoxy]propyl]-4-(phthaloylamino)butylamide (2.00 g) in ethanol (30 ml) was added hydrazine hydrate (80%) (0.40 g). The resulting mixture was refluxed for 2 hours. The reaction mixture was concentrated under reduced pressure, and to the residue was added chloroform followed by stirring for a while and filtration. The filtrate was concentrated under reduced pressure.

The residue was then dissolved in chloroform (30 ml), and to the solution was added (3,4-methylenedioxy)phenyl isothiocyanate (0.78 g). The mixture was stirred at room temperature for 16 hours. The reaction mixture was concentrated under reduced pressure, and the residue extracted with chloroform. An organic layer was washed with water and a saturated aqueous saline solution, then dried over anhydrous sodium sulfate and concentrated under reduced pressure.

The residue was subjected to column chromatography methanol (20:1) was obtained 1.81 g of 1-[3-[N-[3-[3(piperidinomethyl)phenoxy]propyl]carbamoyl]-propyl]-3-[(3,4methylenedioxy)phenyl] thiourea. Spectroscopic data of the product support a structure of the formula (IV).

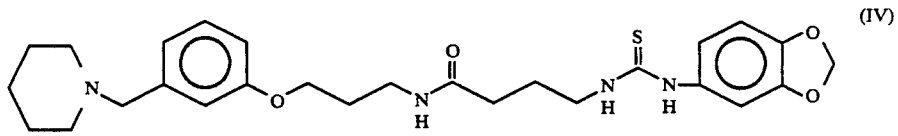

NMR(CDCl$_3$) δ: 1.3–2.6(16H, m), 3.2–3.8(6H, m), 4.00(2H, t, J=6Hz), 5.95(2H, s), 6.5–7.5(8H, m)

EXAMPLE 2

The procedures of Example 1 were repeated using (3,4-ethylenedioxy)phenyl isothiocyanate in place of the (3,4-methylenedioxy)phenyl isothiocyanate used therein. There was obtained 1-[3-[N-[3-[3-(piperidinomethy)phenoxy]propyl]carbamoyl]propyl]-3-[(3,4-ethylenedioxy)phenyl]thiourea. Spectroscopic data of the product support a structure of the formula (V).

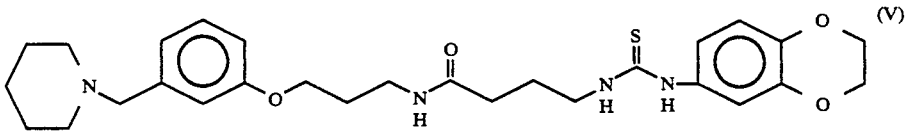

NMR(CDCl$_{13}$) δ: 1.3–2.6(16H, m), 3.2–3.8(6H, m), 4.00(2H, t, J=6Hz), 4.20(4H, bs), 6.5–7.5(8H, m)

EXAMPLE 3

The procedures of Example 1 were repeated using N-[3-[3-(pyrrolidinomethyl)phenoxy]propyl]-4-(phthaloylamino in place of N-[3-[3-(piperidinomethyl)phenoxy]propyl]-4-(phthaloyamino)butylamide used therein. There was obtained 1-[3-[N-[3-[3-(pyrrolidinomethyl)phenoxy]propyl]carbamoyl]propyl]-3-[(3,4-methylenedioxy)phenyl]-thiourea. Spectroscopic data of the product support a structure of the formula (VI).

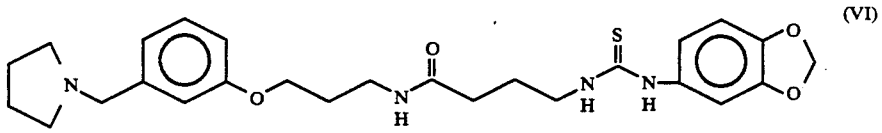

NMR(CDCl$_3$) δ: 1.3–2.7(14H, m , 3.2–3.8(6H, m), 4.00(2H, t, J=6Hz), 5.96(2H, s), 6.5–7.5(8H, m)

EXAMPLE 4

The procedures of Example 1 were repeated using N-3-[3-((3-methylpiperidino)methyl)phenoxy]propyl]-4(pht aloylamino)butylamide in place of N-[3-[3-(piperidinomethyl)phenoxy]propyl]-4-(phthaloylamino)-butylamide used therein. There was obtained 1-[3-[N-[3-[3((3-methylpiperidino)methyl)-phenoxy]propyl]carbamoyl]propyl]-3-[(3,4-methylenedioxy)phenyl]thiourea. Spectroscopic data of the product support a structure of the formula (VII).

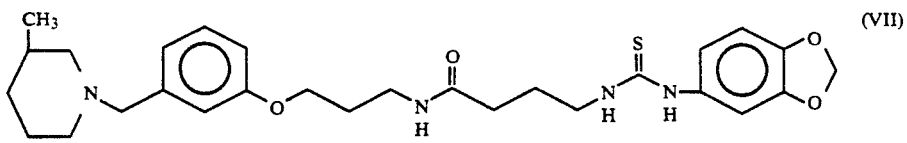

NMR(CDCl₃) δ:0.7–2.7(18H, m), 3.2–3.8(6H, m), 3.98(2H, t, J=6Hz), 5.96(2H, s), 6.5–7.5(8H, m)

EXAMPLE 5

The procedures of Example 1 were repeated using N-[3-[3-(diethylaminomethyl)phenoxy]propyl]-4-(phthaloylamino)butylamid in place of N-[3-[3(piperidinomethyl)phenoxy]-butylamide used therein. There was obtained 1-[3-[N-[3-[3-(diethylaminomethyl)phenoxy]propyl]carbamoyl]propyl]-3-[(3,4-methylenedioxy)phenyl]thiourea. Spectroscopic data of the product support a structure of the formula (VIII).

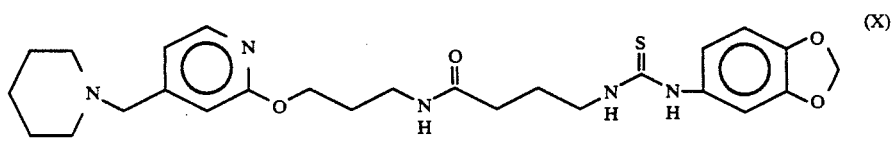

NMR(CDCl₃) δ: 1.05(6H, t, J=7Hz), 6–2.5(6H, m), 2.54(4H, q, J=7Hz), 3.2—3.8(6H, m), 3.98(2H, t, J=6Hz), 5.96(2H, s), 6.5–7.5(8H, m)

EXAMPLE 6

The procedures of Example 1 were repeated using N-[3-3-(piperidinomethyl)phenoxy]propyl]-6-(phthaloylamino)-hexylamide in place of N-[3-[3-(piperidinomethyl)phenoxy]-propyl]-4-(phthaloylamino)butylamide used therein. There was obtained 1-[5-[N-[3-[3-(piperidinomethyl)phenyl]-propyl] carbamoyl][pentyl]-3-[(3,4-methylenedioxy)-phenyl]-thiourea. Spectroscopic data of the product support a structure of the formula 1(IX).

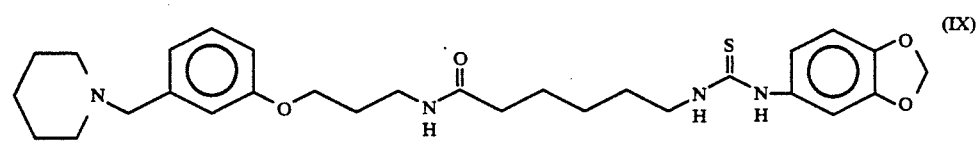

NMR(CDCl₃) δ: 1.3–2.7(22H, m), 3.2–3.8(6H, m), 4.00(2H, t, J=6Hz), 5.96(2H, s), 6.5–7.5(8H, m)

EXAMPLE 7

The procedures of Example 1 were repeated using N-[3-[4-(piperidinomethyl)pyridin-2-oxy] propyl]-4-used therein. There was obtained 1-]3-]N-]3-]4-(piperidinomethyl)pyridin-2-oxy] propyl] carbamoyl] proxyl]-3-[(3,4-methylenedioxy)phenyl] thiourea. Spectroscopic data of the product support a structure of the formula (X).

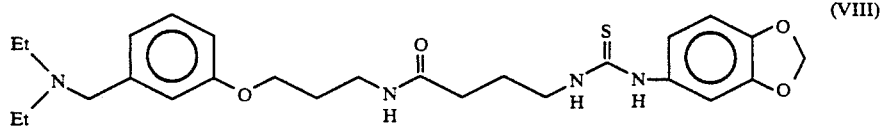

NMR(CDCl₃) δ: 1.3–2.7(6H, m), 4.00(2H, t, J=6Hz), 5.96(2H, s), 6.5–7.0(8H, m), 8.00(1H, d, J=5Hz), 8.37(1H, bs)

EXAMPLE 8

The procedures of Example 1 were repeated using (3,4-ethylenedioxy)benzyl isothiocyanate in place of (3,4-methylenedioxy)phenyl isothiocyanate used therein. There was obtained 1-[3-[N-[3-3-(piperidinomethyl)phenoxy]-propyl] carbamoyl]0 propyl]-3-[(3,4-ethylenedioxy)-benzyl] thiourea. Spectroscopic data of the product support a structure of the formula (XI).

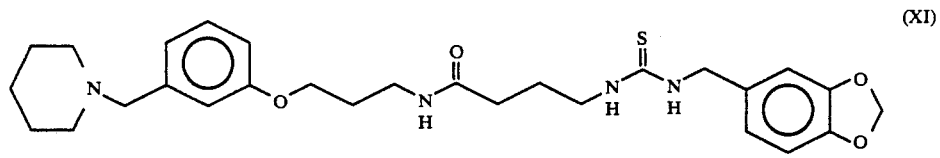

NMR(CDCl₃) δ: 1.3–2.6(16H, m), 3.2–3.8(6H, m) 4.00(2H, t, J=6Hz), 4.80(2H, d, J=5Hz), 6.00(2H, s), 6.5–7.5(8H, m)

TEST EXAMPLE 1

Inhibitory Action Against Peptic Ulcer Induced By Water Immersion Restrain Stress SD male rats (weighing 200–300 g) were fasted for 24 hours before oral administration of a thiourea derivative of the invention at a dose of 32 mg/kg bodyweight. One hour later, the animal was put in a stress cage and loaded with water immersion restraint stress in a water bath at 23° C.

Seven hours after loading with the stress, the rat was sacrificed with ether, and the stomach was excised and treated with formalin. Area (mm$^2$) of the lesions developed in the glandular stomach area was then measured. Results were expressed in sum of the lesions per animal which was referred to as peptic ulcer index. The results are shown in Table 1.

As apparent from Table 1, the compounds of the invention had a high antiulcer activity. It was confirmed that the thiourea derivatives of the invention not shown in the table also have a similar antiulcer activity.

Percent inhibition of the peptic ulcer formation (%) as shown in the table was calculated according to the following equation:

$$\text{Percent inhibition of the peptic ulcer formation}(\%) = \left(1 - \frac{\text{Ulcer index for rats orally receiving a thiourea derivative of the invention}}{\text{Ulcer index for rats not receiving a thiourea derivative of the invention}}\right) \times 100$$

TEST EXAMPLE 2

Inhibitory Action Against Ethanol Peptic Ulcer

SD male rats (weighing 200–300 g) were fasted for 24 hours before oral administration of a thiourea derivative of the invention at a dose of 32 mg/kg bodyweight. One hour later, ethanol was orally given in a volume of 0.5 ml/100 g bodyweight. One hour after administering ethanol, the rat was sacrificed with ether, and the stomach was excised and treated with formalin. Area (mm$^2$) of the lesions developed in the glandular stomach area was then measured. Results were expressed in sum of the lesions per animal which was referred to as peptic ulcer index. The results are shown in Table 1.

As apparent from Table 1, the compounds of the invention had a high antiulcer activity. It was confirmed that the thiourea derivatives of the invention not shown in the table also have a similar antiulcer activity.

Percent inhibition of the peptic ulcer formation (%) as shown in the table was calculated according to the same equation as mentioned above.

TEST EXAMPLE 3

Antimicrobial Activity Against *Helicobacter Pylori*

Antimicorbial activity of the thiourea derivatives according to the invention against *Helicobacter pylori* (or *Campylobacter pylori*) was evaluated by employing strain NCTC 11916 as a Helicobacter test organism and determining MIC (minimum inhibitory concentration) of the thiourea derivative against *Helicobacter pylori*.

The *Helicobacter pylori* was pre-incubated in a plate medium for 3–5 days. The medium was prepared by dissolving 38 g of a Mueller-Hinton medium (manufactured by Difco) in an appropriate amount of distilled water, sterilizing the solution in an autoclave, adding to the solution 50 ml of a horse hemolysis solution (manufactured by Nippon Seibutu Zairyou Center: Horse defibrinized blood, hemolyzed by a lyophilization treatment) and 2 ml of Skirrow, a Campylobacter selective supplement (manufactured by OXOID) containing vancomycin (5 mg), trimethoprim (2.5 mg) and polymyxin B (1250 IU) per vial (2 ml), and further an appropriate amount of distilled water to a volume of 1 L in total and expanding and solidifying the solution on a dish. These antibiotics were contained for inhibition of the growth of microorganisms with than *Helicobacter pylori*.

The *Helicobacter pylori* pre-incubated under slightly aerobic conditions (an $O_2$ concentration of about 5%) at 37° C. for 3–5 days was suspended in a physiological saline solution in a concentration of approximately $10^8$ organisms/ml. Approximately 10–20 µl of the suspension was inoculated on a medium for MIC measurement in cross streaks. The medium for MIC measurement was prepared by mixing a solution of the same composition as that of the medium for pre-incubation with a solution of a thiourea derivative according to the invention in DMSO (dimethylsulfoxide; a final concentration of 2.5% or below) at a ratio of 9:1 and solidifying the mixture on a dish. The DMSO solution was formed by the twofold dilution method using sterilized distilled water. As in the pre-incubation, the *Helicobacter pylori* was cultured under slightly aerobic conditions at 37° C. for 3–5 days. After completion of the culture, growth of the microorganisms on the streaks was visually determined. The minimum concentration of the thiourea derivative in which no growth was observed was taken as MIC. The MIC of cemetidine, an antagonist to histamine was also measured for comparison. The results are shown in Table 1.

As apparent from Table 1, the compounds of the invention possessed a marked antimicrobial activity. It was confirmed that the thiourea derivatives of the invention not shown in the table also have a similar antimicrobial activity.

TABLE 1

| | Test Example | | |
|---|---|---|---|
| | Inhibitory action against stress peptic ulcer (Test Example 1) Percent inhibition of p.u.* formation (%) | Inhibitory action against ethanol peptic ulcer (Test Example 2) Percent inhibition of p.u.* formation (%) | Antimicrobial activity against *Helicobacter pylori* (Test Example 3) MIC (µg/ml) |
| Example | | | |
| 1 | 80 | 67 | 6.25 |
| 2 | 76 | 66 | 6.25 |
| 3 | 68 | 61 | 6.25 |
| 4 | 77 | 71 | 6.25 |
| 5 | 62 | 52 | 12.5 |
| 6 | 65 | 70 | 6.25 |
| 7 | 78 | 63 | 6.25 |
| 8 | 82 | 78 | 6.25 |
| Cemetidine | 64 | 16 | ≧400 |

*peptic ulcer

ACUTE TOXICITY

An acute toxicity test was carried out with ICR male mice (5 weeks old) by oral administration. $LD_{50}$ was 1000 mg/kg or higher with any of the compounds of the invention thereby demonstrating high safety as compared with the effective dose.

According to the present invention, there are provided novel thiourea derivatives and an antimicrobial agent and an antipeptic ulcer agent containing the same. It was demonstrated that the above-mentioned compounds of the invention possess high antiulcer activities. Thus, they can effectively be used as a therapeutic agent for peptic ulcers since they promote cure of the peptic ulcers by inhibition of gastric secretion, and additionally, they can prevent the recurrence after discontinuation of the administration due to their strong gastric defense factor-reinforcing activity as well as their antimcirobial activity against *Helicobacter pylori*.

What is claimed is:

1. A thiourea derivative represented by the general formula (I)

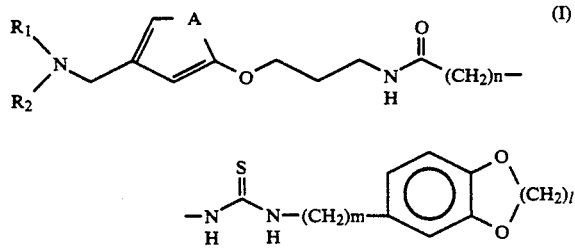

wherein $R_1$ and $R_2$ are the same or different and each represents a lower alkyl group, or $R_1$ and $R_2$ taken together represent a group having the formula —$(CH_2)_x$—$CHR_3$—$(CH_2)_y$— in which $R_3$ represents hydrogen or a lower alkyl group and x and y represent an integer of 0 to 2, respectively, A represents the formula —CH=CH— or —CH'N—, 1 is 1 or 2, m represents an integer of 0 to 2 and n represents an integer of 1 to 5 or physiologically acceptable salt thereof.

2. The thiourea derivative according to claim 1 wherein $R_1$ and $R_2$ taken together represent a group having the formula —$(CH_2)_x$—$CHR_3$—$(CH_2)_y$— in which $R_3$ is a hydrogen atom or a methyl group, x and y are 1 or 2, respectively, A represents the formula —CH=CH—, 1 is 1 or 2, m is 0 or 1 and n is 3 or 5 or physiologically acceptable salt thereof.

3. The thiourea derivative according to claim 1 wherein $R_1$ and $R_2$ taken together represent a group having the formula —$(CH_2)_x$—$CHR_3$—$(CH_2)_y$— in which $R_3$ is a hydrogen atom, x and y are 2, respectively, A represents the formula —CH=N—, 1 is 1, m is 0 and n is 3 or physiologically acceptable salt thereof.

4. The thiourea derivative according to claim 1 wherein $R_1$ and $R_2$ are ethyl group, respectively, A represents the formula —CH=CH—, 1 is 1, m is 0 and n is 3 or physiologically acceptable salt thereof.

5. An antimicrobial agent against *Helicobacter pylori* comprising an antimicrobially effective amount of the thiourea derivative or physiologically acceptable salt thereof according to claim 1 in combination with a pharmaceutically acceptable carrier or excipient.

6. An antiulcer agent comprising an antiulcer effective amount of the thiourea derivative or physiologically acceptable salt thereof according to claim 1 in combination with a pharmaceutically acceptable carrier or excipient.

7. An antimicrobial agent against *Helicobacter pylori* comprising an antimicrobially effective amount of the thiourea derivative or physiologically acceptable salt thereof according to claim 2 in combination with a pharmaceutically acceptable carrier or excipient.

8. An antimicrobial agent against *Helicobacter pylori* comprising an antimicrobially effective amount of the thiourea derivative or physiologically acceptable salt thereof according to claim 3 in combination with a pharmaceutically acceptable carrier or excipient.

9. An antimicrobial agent against *Helicobacter pylori* comprising an antimicrobially effective amount of the thiourea derivative or physiologically acceptable salt thereof according to claim 4 in combination with a pharmaceutically acceptable carrier or excipient.

10. An antiulcer agent comprising an antiulcer effective amount of the thiourea derivative or physiologically acceptable salt thereof according to claim 2 in combination with a pharmaceutically acceptable carrier or excipient.

11. An antiulcer agent comprising an antiulcer effective amount of the thiourea derivative or physiologically acceptable salt thereof according to claim 3 in combination with a pharmaceutically acceptable carrier or excipient.

12. An antiulcer agent comprising an antiulcer effective amount of the thiourea derivative or physiologically acceptable salt thereof according to claim 4 in combination with a pharmaceutically acceptable carrier or excipient.

13. A method for treating *Helicobacter pylori* infection in a *Helicobacter pylori* infected subject comprising administration of an antimicrobially effective amount of the thiourea derivative or physiologically acceptable salt thereof according to claim 1.

14. A method for treating *Helicobacter pylori* infection in a *Helicobacter pylori* infected subject comprising administration of an antimicrobially effective amount of the thiourea derivative or physiologically acceptable salt thereof according to claim 2.

15. A method for treating *Helicobacter pylori* infection in a *Helicobactor pylori* infected subject comprising administration of an antimicrobially effective amount of the thiourea derivative or physiologically acceptable salt thereof according to claim 3.

16. A method for treating *Helicobacter pylori* infection in a *Helicobacter pylori* infected subject comprising administration of an antimicrobially effective amount of the thiourea derivative or physiologically acceptable salt thereof according to claim 4.

17. A method for treating ulcers comprising administering to a subject suffering from an ulcer an antiulcer effective amount of the thiourea derivative or physiologically acceptable salt thereof according to claim 1.

18. A method for treating ulcers comprising administering to a subject suffering from an ulcer an antiulcer effective amount of the thiourea derivative or physiologically acceptable salt thereof according to claim 2.

19. A method for treating ulcers comprising administering to a subject suffering from an ulcer an antiulcer effective amount of the thiourea derivative or physiologically acceptable salt thereof according to claim 3.

20. A method for treating ulcers comprising administering to a subject suffering from an ulcer an antiulcer effective amount of the thiourea derivative or physiologically acceptable salt thereof according to claim 4.

* * * * *

UNITED STATES PATENT AND TRADEMARK OFFICE
CERTIFICATE OF CORRECTION

PATENT NO. : 5,214,053                                   Page 1 of 3

DATED     : May 25, 1993

INVENTOR(S) : Keiichi NAKAZAWA et al

It is certified that error appears in the above-identified patent and that said Letters Patent is hereby corrected as shown below:

In Column 1, line 24, before "attention", insert -- patients encountered with the recurrence. Consequently, --.

In Column 3, line 66, before "methanol", insert -- on silica gel, and from a fraction eluted with chloroform- --.

In Column 4, line 20, delete "(piperidinomethy)" and insert -- piperidinomethyl --.

In Column 4, line 34, delete "NMR(CDCl$_1$3" and insert -- NMR(CDCl$_3$) --.

In Column 4, line 40, delete "(phthaloylamino" and insert -- (phthaloylamino)butylamide --.

In Column 4, line 41, delete "(phthaloyamino)butylamide" and -- (phthaloylamino)butylamide --.

In Column 4, line 57, delete "1.3-2.7(14H, m," and insert -- 1.3-2.7(14H, m), --.

In Column 4, line 61, delete "N-3-[3-" and insert -- N-[3-[3- --.

In Column 4, line 62, delete "4(pht aloylamino)butylamide" and insert -- 4(phthaloylamino)butylamide --.

In Column 5, line 15, delete "(phthaloylamino)butylamid" and insert -- (phthaloylamino)butylamide --.

In Column 5, line 16, after "[3(piperidinomethyl)phenoxy]" and insert -- propyl]-4-(phthaloylamino) --.

In Column 5, line 36, delete "6-2.5(6H, m)," and insert -- 1.6-2.5(6H, m), --.

UNITED STATES PATENT AND TRADEMARK OFFICE
CERTIFICATE OF CORRECTION

PATENT NO. : 5,214,053
DATED : May 25, 1993
INVENTOR(S) : Keiichi NAKAZAWA et al It is certified that error appears in the above-indentified patent and that said Letters Patent is hereby corrected as shown below:

In Column 5, line 41, delete "N-[3-3-" and insert -- N-[3-[3 --.

In Column 5, line 53, delete "phenyl]" and insert -- phenoxy] --.

In Column 6, line 13, before "used", insert -- (phthaloylamino)butylamide in place of N-[3-[3-(piperidinomethyl)phenoxy]propyl]-4-(phthaloylamino)butylamide --.

In Column 6, line 13, delete "1-]3-]N-]3-]4-" and insert -- 1-[3-[N-[3-[4- --.

In Column 6, line 25, delete "1.3-2.7(6H, m)," and insert -- 1.3-2.7(14H, m), 3.2-3.8(6H, m), --.

In Column 6, line 41, delete "carbamoyl]0" and insert -- carbamoyl] --.

In Column 8, line 5, delete "with" and insert -- other --.

In Column 8, line 43, delete "/ml)" and insert -- ml) --.

In Column 9, line 26, delete "-CH'N-" and insert -- -CH=N- --.

UNITED STATES PATENT AND TRADEMARK OFFICE
CERTIFICATE OF CORRECTION

PATENT NO. : 5,214,053

DATED : May 25, 1993

INVENTOR(S) : Keiichi Nakazawa, et al.

It is certified that error appears in the above-identified patent and that said Letters Patent is hereby corrected as shown below:

In column 9, line 26, delete "-CH'N- and insert -- CH=N- --.

Signed and Sealed this

Eleventh Day of January, 1994

Attest:

BRUCE LEHMAN

Attesting Officer  Commissioner of Patents and Trademarks